United States Patent [19]

van Leusen et al.

[11] Patent Number: 4,548,749
[45] Date of Patent: Oct. 22, 1985

[54] PROCESS FOR THE PREPARATION OF 21-HYDROXY-20-KETO-$\Delta^{16}$-STEROIDS AND NEW INTERMEDIATE COMPOUNDS FORMED IN THIS PROCESS

[75] Inventors: Albert M. van Leusen, Groningen; Adriaan M. van Leusen, Winsum, both of Netherlands

[73] Assignee: Gist-Brocades N.V., Delft, Netherlands

[21] Appl. No.: 604,735

[22] Filed: Apr. 27, 1984

[30] Foreign Application Priority Data

Apr. 29, 1983 [EP] European Pat. Off. ........ 83200618.3

[51] Int. Cl.[4] ................................................. C07J 9/00
[52] U.S. Cl. ............................... 260/239.5; 260/397.5; 260/397.45; 260/397.47; 260/397.3; 260/239.55 C

[58] Field of Search ....................................... 260/239.5

[56] References Cited

U.S. PATENT DOCUMENTS 4,460,509   7/1984   Mosbach et al. ................. 260/239.5

Primary Examiner—Elbert L. Roberts
Attorney, Agent, or Firm—Bierman, Peroff & Muserlian

[57] ABSTRACT

A novel process for the preparation of 21-hydroxy-20-keto-$\Delta^{16}$-steroids comprising reacting a 17-(isocyanosulfonylmethylene)-steroid with an aldehyde and an alcohol to form a 17-(2-alkoxy-3-oxazolin-4-yl)-$\Delta^{16}$-steroid and subjecting the latter to hydrolysis to obtain the corresponding 21-hydroxy-20-keto-$\Delta^{16}$-steroid which are useful to prepare corticoid steroids and novel intermediates.

30 Claims, No Drawings

PROCESS FOR THE PREPARATION OF 21-HYDROXY-20-KETO-Δ16-STEROIDS AND NEW INTERMEDIATE COMPOUNDS FORMED IN THIS PROCESS

STATE OF THE ART

Steroids are used on a large scale as the active ingredients of many types of pharmaceutical compositions and depending on the substituent pattern of the carbon-skeleton, the steroids can be divided into a number of main classes. An important main class of steroids is formed by the cortico-steroids whose natural representatives are usually produced by the adrenal gland. Corticosteroids are characterized by the presence of a 3-keto group, a Δ4-double bond, an 11β-hydroxy group, a 17α-hydroxy group and a 17β-hydroxy-acetyl side chain.

For a long time, corticosteroids were made by chemical degradation of gall acids such as cholic acid, desoxycholic acid and glycocholic acid. Afterwards, hecogenin which could be isolated from plants, particularly from numerous Agave species, became an important raw material too. Since the possibility of the introduction of an 11-hydroxy group by microbiological methods diosgenin which could be isolated from numerous Dioscoreacaea species and stigmasterol, usually isolated from the phytosterol mixtures from soya or calabar beans, have become the most important raw material for the preparation of corticosteroids.

Much attention has been given to new, cheaper raw materials for the synthesis of pharmaceutically active steroids. Therefore, the degradation of the abundant soya bean derived sterols, sitosterol and campesterol by microbiological methods into 17-oxo-steroids was extensively investigated and as a result thereof, 17-oxo-steroids are readily available now at low prices which makes these compounds, together with the possibility of the introduction of an 11-hydroxy group by microbiological methods, ideal starting materials for corticosteroid synthesis.

A number of chemical synthesis for the construction of the corticosteroid side chain from 17-oxo-steroids is known. For instance, J. Org. Chem., Vol. 44, p. 1582 (1979) describes a method which uses asulfenate-sulfoxide rearrangement for the introduction of the 17-(dihydroxyacetone) side chain. Another route is described in J.C.S. Chem. Comm., 1981, p. 775 in which the reaction of 17-oxo-steroids with ethyl isocyanoacetate is described followed by a number of other reactions, which ultimately result in the dihydroxyacetone side chain of corticosteroids. Other synthesis of the corticosteroid side chain or of compounds which can be used as precursors therefore are described in J.C.S. Chem. Comm., 1981, p. 774, J.C.S. Chem. Comm., 1982, p. 551, Chem. Ber., Vol. 113, p. 1184 (1980), and J. Org. Chem., 1982 p. 2993.

OBJECTS OF THE INVENTION

It is an object of the invention to provide a novel process for the preparation of 21-hydroxy-20-keto-Δ16-and certain novel steroids.

It is further object of the invention to provide novel 17-(2-alkoxy-3-oxazolin-4-yl)-Δ16-steroids and a novel process for their preparation.

These and other objects and advantages of the invention will become obvious from the following detailed description.

THE INVENTION The novel process of the invention for the preparation of 21-hydroxy-20-keto-Δ16-steroids comprises reacting a 17-(isocyanosulfonylmethylene)-steroid with an aldehyde and an alcohol to form a 17-(2-alkoxy-3-oxazolin-4-yl)-Δ16-steroid and subjecting the latter to hydrolysis to obtain the corresponding 21-hydroxy-20-keto-Δ16-steroid.

In a preferred mode of the process, the starting 17-(isocyanosulfonylmethylene)-steroid has the formula

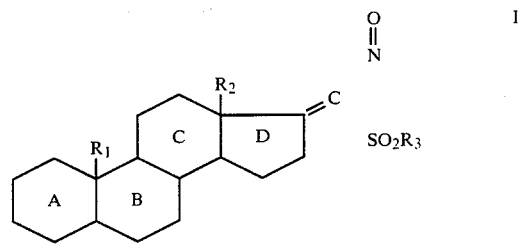

wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 6 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms.

The preparation of the compounds of formula I is described in commonly assigned U.S. patent application Ser. No. filed on even date herewith (attorney's docket No. 253,087) entitled "Novel 17-substituted steroids" by reacting a 17-keto-steroid with a sulfonylmethylisocyanide to form the corresponding 17-(formamidosulfomethylene)-steroid which is dehydrated to form the corresponding isocyanide of formula I.

The process of the invention may be illustrated by the following equation:

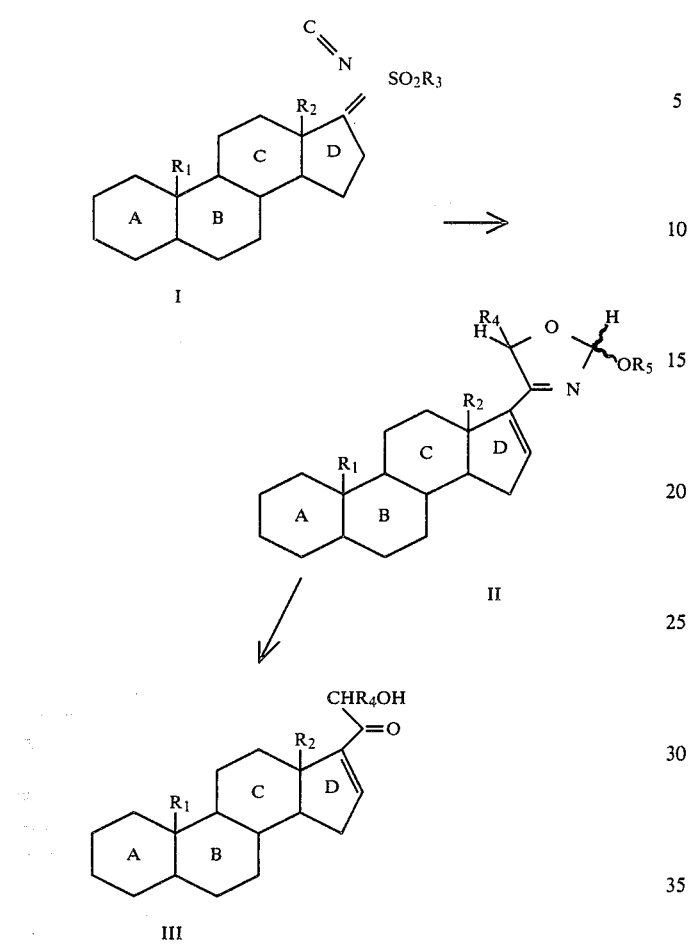

Examples of $R_3$ are alkyl of 1 to 10 carbon atoms such as methyl, ethyl, isopropyl, n-butyl and octyl; dialkylamino with alkyls of 1 to 8 carbon atoms, preferably 1 to 4 carbon atoms, such as dimethylamino or diethylamino; heterocycle of up to 8 ring atoms optionally containing an oxygen ring atom such as pyrrolidine and morpholine; and aryl such as phenyl or naphthyl optionally substituted with at least one member of the group consisting of halogen and alkyl and alkoxy of 1 to 6 carbon atoms such as phenyl, p-methoxyphenyl and p-methylphenyl.

When the rings A,B,C and D contain one or more double bonds, the double bonds are preferably present between $C_1$ and $C_2$, $C_3$ and $C_4$, $C_4$ and $C_5$, $C_5$ and $C_6$, $C_6$ and $C_7$, $C_9$ and $C_{10}$, $C_9$ and $C_{11}$ and/or $C_{11}$ and $C_{12}$. More preferably, the double bond is between $C_4$ and $C_5$ and/or $C_9$ and $C_{11}$. When two or more double bonds are present, the following systems are especially preferred: $C_3(C_4)$ and $C_5(C_6)$, $C_4(C_5)$ and $C_6(C_7)$, $C_1(C_2)$ and $C_4(C_5)$, $C_1(C_2)$, $C_3(C_4)$ and $C_5(C_{10})$ and $C_1(C_2)$, $C_4(C_5)$ and $C_6(C_7)$. Preferably, there is also a double bond between $C_9$ and $C_{11}$.

When the rings A,B,C and D are substituted with hydroxy, suitable substituents are 3-, 9-, 11-, 12- or 14-hydroxy, preferably a 3- or 9-hydroxy. When the rings A,B,C and D are substituted with an amino, suitable aminos are 3-alkylaminos preferably containing 1–4 carbon atoms, 3-dialkylamino groups wherein the alkyls are the same or different and each alkyl preferably contains 1–4 carbon atoms, or amino groups in which the nitrogen atom together with the alkyls form a heterocyclic ring, preferably containing 1–8 ring atoms which ring optionally may contain an oxygen atom. Particularly preferred are dimethylamino, diethylamino, pyrrolidine and morpholine.

When the rings A,B,C and D are substituted with an oxygen atom, the oxygen atom is preferably present at $C_3$, $C_{11}$ or $C_{12}$. When the rings A,B,C and D are substituted with a halogen, suitable halogens are 6-, 9- or 11-fluorine, chlorine or bromine atoms, preferably 6- or 9-fluorine or chlorine atoms.

When the rings A,B,C and D are substituted by an alkyl, suitable alkyls are 1-, 2-, 6-, 7- or 16-methyl, preferably 1- or 6-methyl. When the rings A,B,C and D are substituted by an alkoxy, suitable alkoxys are 3-, 9-, 11- or 12-alkoxy containing 1–4 carbon atoms, preferably 3-, 9- or 11-methoxy or ethoxy groups. When the rings A,B,C and D are substituted by an alkoxyalkoxy, suitable groups are 3- or 11-methoxymethoxy, methoxyethoxy or tetrahydropyranyloxy. When the rings A,B,C and D are disubstituted, suitable substituents are epoxy groups at $C_1$ and $C_2$ or $C_9$ and $C_{11}$ or a methylene group attached to $C_1$ and $C_2$ or a 3,3-alkylenedioxy, a 3,3-alkylenedithio or a 3,3-alkyleneoxythio group. The alkylene group preferably contains 2 or 3 carbon atoms.

More particularly, the invention relates to compounds in which $R_1$ and $R_2$ are methyl or in which $R_1$ is absent, which are substituted by halogen, especially fluorine or hydroxy at $C_9$ and a hydroxy or keto group at $C_{11}$, or containing functional groups such as a double bond or epoxy group between $C_9$ and $C_{11}$, which can be converted by methods known in the art into the groups mentioned before, and which contain a keto group at $C_3$ and double bonds between $C_1$ and $C_2$ and/or $C_4$ and $C_5$, or containing functional groups which can be converted into the keto group and double bonds mentioned above.

The novel process of the invention for the preparation of the 17-(2-alkoxy-3-oxazolin-4-yl)-$\Delta^{16}$-steroids of formula II comprises reacting the 17-(isocyanosulfonylmethylene)-steroids with an aldehyde and an alcohol under basic conditions.

The reaction can be carried out in an inert organic solvent to which a base is added. Examples of suitable organic solvents are methylene chloride, chloroform, 1,2-dichloroethane, benzene, toluene, chlorobenzene, dioxane, bis-(2-methoxyethyl)-ether, 1,2-dimethoxyethane, tetrahydrofuran or mixtures thereof. As the first step and the second step may be performed in a one-pot-reaction, preferably a solvent is used in which also the hydrolysis can be carried out.

Suitable bases which can be used are metal hydroxides and quaternary ammonium and phosphonium hydroxides, preferably alkali metal hydroxides such as potassium hydroxide, and quaternary ammonium hydroxides such as triethylbenzylammonium hydroxide. Also alkali metal alcoholates such as potassium butoxide may be used. The reaction can be carried out at a temperature between 0° and 100° C., preferably between 0° and 30° C. Sometimes it may be necessary to add a catalyst to the reaction mixture in the form of a quaternary ammonium or phosphonium salt, for instance trimethylbenzyl ammonium halide, triethylbenzyl ammonium halide, tetrabutyl ammonium halide and alkyl triaryl phosphonium halide. Also crown ethers such as 15-crown-5 or 18-crown-6 can be used.

Suitable reaction conditions also include phase transfer-conditions, i.e. a two phase system of an organic layer and an aqueous layer to which an amount of a phase transfer catalyst salt has been added. The reaction can be carried out at temperatures between 0° and 100° C., preferably between 0° and 30° C. See for a general survey of phase-transfer reactions E. V. Dehmlov and S. S. Dehmlov, Phase Transfer Catalysis, Weinheim Chemie, 1980.

Suitable organic solvents for the organic layer are methylene chloride, chloroform, 1,2-dichloroethane, benzene, toluene, chlorobenzene and dichlorobenzene. In general, all those organic solvents can be used which are immiscible with water, and in which the relevant compounds are soluble.

Suitable aqueous layers are solutions of alkali metal hydroxides in water, for example a 5-50% solution of lithium hydroxide, sodium hydroxide or potassium hydroxide. Suitable phase transfer catalysts are quaternary ammonium and phosphonium salts and crown-ethers, for instance trimethylbenzyl ammonium halide, triethyl benzyl ammonium halide, tetrabutyl ammonium halide, alkyl triaryl phosphonium halides, 15-crown-5 and 18-crown-6.

Examples of aldehydes which can be used in the reaction are arylaldehydes, alkylaldehydes and formaldehyde. Suitable aldehydes are phenylaldehydes in which the phenyl group optionall is substituted by at least one halogen, alkyl or alkoxy, alkyl aldehydes in which the alkyl has 1-4 carbon atoms and optionally is substituted by at least one halogen or alkoxy. Preferred aldehydes are benzaldehyde, acetaldehyde and formaldehyde, more particularly formaldehyde. Formaldehyde is used either as formaline (solution in water), as paraformaldehyde or as trioxane.

Suitable alcohols are alkyl alcohols and arylalkyl-alcohols. Preferred alkyl alcohols are alcohols of 1 to 6 carbon atoms such as methanol, ethanol and allyl alcohol. Also alkoxyalkyl alcohols such as methoxymethanol can be used. A preferred arylalkyl alcohol is benzyl alcohol. In general, all alcohols can be used which do not interfere in the reaction and preferably methanol or ethanol is used.

The hydrolysis of the oxazolinyl compound of formula II to the 21-hydroxy-20-keto-$\Delta^{16}$-steroid of formula III can be carried out in an organic solvent using an acidic aqueous solution. Suitable organic solvents are, for instance, diethyl ether, methanol and tetrahydrofuran. Suitable acids are dilute strong acids such as hydrogen chloride, sulfuric acid and phosphoric acid. Also, acetic acid and formic acid can be used. While the two reaction can be separately effected, it is preferred that the two reactions are combined into a so-called "one-pot process".

It is observed that sometimes not only is the oxazolinyl group hydrolyzed but also other groups linked to the steroid skeleton. These groups may have had the function of protective groups (compare what is stated on protective groups in the simultaneously filed application entitled "17-(isocyano-sulfonylmethylene)-steroids and 17-(formamido-sulfonylmethylene)-steroids and their preparation."

The invention comprises also 21-hydroxy-20-keto-delta-$^{16}$-steroids as described above as far as these latter compound are novel.

In the following examples there are described several preferred embodiments to illustrate the invention and it is to be understood that the invention is not intended to be limited to the specific embodiments. Triton B used in the examples is a 40% solution of benzyltrimethylammonium hydroxide in methanol and THF is tetrahydrofuran.

EXAMPLE 1a 3-methoxy-17-(2-methoxy-3-oxazolin-4-yl)-$\Delta^{3,5,16}$-androstatriene 239 mg (0.5 mmol)of 3-methoxy-17-(isocyano-p-methylphenylsulfonylmethylene)-$\Delta^{3,5}$-androstadiene were dissolved in 10 ml of benzene and to this solution were added 0.2 ml of 40% solution in water of formaline, 0.2 ml of methyl, 15 mg of benzyl triethyl ammonium chloride and 4 ml of 50% of aqueous NaOH solution. The mixture was stirred vigorously for one hour at 20° C. and was extracted with benzene. The organic phase was filtered over Al$_2$O$_3$ (act. II-III; layer of 2 cm) followed by washing with 50 ml of methylene chloride and evaporation in vacuo to obtain 170 mg (90% yield) of 3-methoxy-17-(2-methoxy-3-oxazolin-4-yl)-$\Delta^{3,5,16}$-androstatriene.

IR (Neat): 1655, 1630 cm$^{-1}$.

$^1$H NMR (CDCl$_3$) delta 0.8-2.7 (m), 1.0 (s, 6H), 3.27 (s, 3H), 3.49 (s, 3H), 4.62 (m, 2H), 5.08, 5.08 (m, 2H), 6.2 (m, 1H), 6.45 (m, 1H).

The experiment was repeated using instead of benzyltriethylammonium chloride, tetrabutylammonium tetrafluoroborate, tetraethylammonium hydroxide, 18-crown-6 and benzyltriethylammonium hydroxide and the yields were 93%, 83%, 53% and 91% respectively.

EXAMPLE 1b $\Delta^{4,16}$- pregnadiene-21-ol-3,20-dione 170 mg (0.45 mmols) of the product of Example 1a were dissolved in a mixture of 2.5 ml of 8% H$_2$SO$_4$ and 10 ml of THF and after standing at ambient temperature for 18 hours, 10 ml of water were added. The THF was removed by evaporation in vacuo at 20° C., whereafter the precipated solid was collected, washed with water and dried to obtain 149 mg (90% yield) calculated on the isocyanide of $\Delta^{4,6}$-pregnadiene-21-ol-3,20-dione melting at 215°-220° C. (dec; acetone-pet ether 40°-60° C.); $(\alpha)^{20}$+145° (c 1.0, CHCl$_3$);

IR (Nujol): 3350 (OH), 1665 (C=0), 1620 (C=C).

$^1$H NMR (CDCl$_3$): delta 0.8-2.7 (m), 1.0 (s, 3H), 1.2 (s, 3H), 3.68 (s, 1H), 4.4 (s, 2H), 5.65 (s, 1H), 6.68 (m, 1H); Mass: M$^+$328 (calculated 328); (Litt.: Allen et al, J. A. C. S., Vol. 77, p. 1028 (1975), m.p. 227°-232° C.).

EXAMPLE 1c 3-methoxy-17-(2-methoxy-3-oxazol-4-yl)-$\Delta^{3,5,16}$-androstatriene 0.2 ml of formaline and 0.6 ml of Triton B were added to a solution of 240 mg of 3-methoxy-17-(isocyano-p-methylphenylsulfonylmethylene)-$\Delta^{3,5}$-androstadiene in THF under nitrogen. After stirring for 15 minutes, water was added and the mixture was extracted with methylene chloride. After drying over a layer of alumina oxide and evaporation in vacuo, 139 mg (83%) of 3-methoxy-17-(2-methoxy-3-oxazolin-4-yl)-$\Delta^{3,5,16}$-androstatriene were obtained. The compound was identical to the one described in 1a.

The experiment was repeated using instead of Triton B 0.6 ml of tetraethylammonium hydroxide in water and 1 ml of methanol. The yield of 92%. The experiment was repeated using 2 g of powdered KOH as base and tetraybutylammonium tetrafluoroborate was used as catalyst. The yield was 92%. The experiment was repeated using 10 ml of benzene as solvent, 0.65 g of powdered KOH as a base and 0.2 ml of methanol as alcohol. The yield after 1 hour of stirring was 90%. When ethanol was used instead of methanol, the same result was obtained.

EXAMPLE 1d $\Delta^{4,16}$-pregnadiene-21-ol-3,20-dione 239 mg of 3-methoxy-17-(isocyano-p-methylphenyl-sulfonylmethylene)-$\Delta^{3,5}$-androstadiene were dissolved in 10 ml of THF under nitrogen and 0.2 ml of 36% of formaline, 0.2 ml of methanol and 0.8 g of powdered KOH were added. After stirring for 15 minutes, the solution was filtered and 1.5 ml of 4N sulfuric acid were added followed by stirring for 20 hours. 10 ml of water were added, and the THF was evaporated in vacuo. The residue was filtered and the white solid was dried to obtain 123 mg (75% yield) of $\Delta^{4,16}$-pregnadiene-21-ol-3,20-dione. The same reaction was repeated using instead of methanol 0.2 ml of ethanol and the yield was 146 mg (89%).

EXAMPLE 2

3-methoxy-19-nor-$\Delta^{1,3,5(10),16}$-pregnatetraen-21-ol-20-one

To a solution of 461 mg (1 mmol) of 3-methoxy-17-(isocyano-p-methylphenylsulfonylmethylene)-$\Delta^{1,3,5(10)}$estratriene in 20 ml of benzene were added. 300 mg (10.0 mmol) of paraformaldehyde, 0.4 ml of methanol, 23 mg (0.1 mmol) of benzyltriethyl-ammonium chloride and 8 ml of 50% aqueous NaOH solution were added and the mixture was stirred vigorously for one hour and then the organic solvent phase was separated from the water phase and the latter was extracted once with 5 ml of benzene. The combined benzene fractions were filtered over Al$_2$O$_3$ (act. II-III) followed by washing with 100 ml of methylene chloride. After evaporation of the solvent 3-methoxy-17-(2-methoxy-3-oxazolin-4-yl)-19-nor-$\Delta^{1,3,5(10),16}$-estratetraene was obtained as an oil. Without further processing, this oxazolinyl compound was hydrolyzed by dissolving it in 15 ml of THF and 5 ml of 8% H$_2$SO$_4$. After 18 hours storage at room temperature, the THF was evaporated in vacuum at 20° C. and the remaining solid substance was collected, washed with water and dried to obtain 300 mg (92% yield) of 3-methoxy-19-nor-$\Delta^{1,3,5(10),16}$-pregnatetraen-21-ol-20-one melting at 120°-142° C. After two recrystallizations from ether/pet. ether 40°-60° C. (1:4), the melting point of the product was 1-4°-146° C. $(\alpha)^{20}$ 81° (c 1.00 CHCl$_3$).

IR (Nujol): 3550 (OH), 1670 (C=O), 1620 (C=C), 1590 (Ar) cm$^{-1}$.

$^1$H NMR (CDCl$_3$): delta 0.9-3.6 (m), 0.95 (s), 3.71 (s, 3H), 4.42 (s, 2H), 6.53, 6.65, 6.71, 7.02, 7.12 (m, 4H).

Analysis: C$_{21}$H$_{26}$O$_3$; molecular weight=326.44 Calculated: %C 77.27 %H 8.03. Found: 77.1 8.1.

EXAMPLE 3

$\Delta^{1,4,16}$-pregnatriene-21-ol-3,20-dione 461 mg (1.0 mmol) of 17-(isocyano-p-methylphenyl-sulfonylmethylene)-$\Delta^{1,4}$-androstadien-3-one were converted to the hydroxyacetyl compound as described in Example 2 with the difference that during the first reaction step, the benzene solution was stirred for half an hour. The yield was 83% and the melting point was 155°-168° C. After two crystallizations from ether, the melting point of the product was 162°-174° C. $(\alpha)^{20}$+92.5° (c 1.00 CHCl$_3$).

IR (Nujol): 3500 (OH), 1665 (C=O), 1630, 1610, 1590 (C=C) cm$^{-1}$.

$^1$H NMR (CDCl$_3$): 0.8-2.7 (m), 1.00 (s), 1.25 (s), 3.25 (br. 1H), 4.40 (s, 2H), 5.95-6.10 (m, 2H), 6.21, 6.23 (d, 1H), 6.6-6.7 (m, 1H).

Analysis: C$_{21}$H$_{26}$O$_3$; molecular weight=326.439 Calculated: %C 77.27 %H 8.03. Found: 76.7 8.1.

The experiment was repeated under the same conditions except the stirring time of the phase transfer reaction (first reaction step). Stirring for one hour resulted in a yield of 70% and stirring for two hours resulted in a yield of 52%.

EXAMPLE 4

$\Delta^{4,9(11),16}$-pregnatriene-21-ol-3,20-dione 475 mg (1.0 mmol) of 3-methoxy-17-(isocyano-p-methylphenylsulfonyl-methylene)-$\Delta^{3,5,9(11)}$-androstatriene were converted to the hydroxyacetyl compound as described in Example 2. The yield was 300 mg (93%) and the melting point was 180°-193° C. After two crystallizations from methylene chloride/ether (2:7), the melting point of the product was 205°-208° C., $(\alpha)^{20}$+204° (c. 1.00 CHCl$_3$).

IR (Nujol): 3500 (OH), 1675 (C=O), 1620, 1595 (C=C), 1100 cm$^{-1}$.

$^1$H NMR (CDCl$_3$): delta 0.7-3.3 (m), 0.90 (s), 1.37 (s), 3.06 (s), 4.38 (s, 2H), 5.30-5.60 (m, 2H), 5.27 (s), 6.55-5.80 (m, 1H). (Litt.: J.A.C.S. Vol. 77, p. 1028 (1955); m.p. 204°-209° and m.p. 215°-218° $(\alpha)^{20}$+194° (c 1.0, CHCl$_3$).

EXAMPLE 5

$\Delta^{4,16}$-pregnadiene-11$\beta$,21-diol-3,20-dione 493 mg (1.0 mmol) of 3-methoxy-17-(isocyano-p-methylphenylsulfonylmethylene)-$\Delta^{9,16}$-androstadiene-11$\beta$-ol were converted to the hydroxyacetyl compound as described in Example 2 with the difference that the stirring time for the first reaction step was ¾ hour to obtain 233 mg of crude product (68%). After crystallization from acetone-ether (1:3), the $\Delta^{4,16}$-pregnadiene-11$\beta$,21-diol-3,20-dione melted at 148°-153° C., $(\alpha)^{20}$+198° (c 1.0, CHCl$_3$).

IR (Nujol): 3500 (OH), 1690 (C=O), 1655 (br, C=C+C=O) cm$^{-1}$.

$^1$H NMR (CDCl$_3$): delta 0.75-2.9 (m), 1.25 (s), 1.46 (s), 3.0-3.7 (m, 2H), 4.37 (br. s, 3H), 5.57 (s, 1H), 6.48-6.72 (m, 1H). (Litt. J.A.C.S., Vol. 77, p. 1028 (1955); m.p. 154°-156° C., $(\alpha)^{20}$+200° (c 0.47, CHCl$_3$).

It is observed that the yield was improved by a more thorough washing with CH$_2$Cl$_2$. $^1$H NMR of the intermediate 3-methoxy-1-17-(2-methoxy-3-oxazolin-4-yl)-$\Delta^{3,5,16}$-androstatriene-11$\beta$-ol: (CDCl$_3$): delta 0.7-2.9 (m), 1.23 (s, 3H), 1.28 (s, 3H), 3.27 (s, 3H), 3.48 (s, 3H), 4.25 (s, 1H), 4.61 (m, 2H), 5.00 (m, 2H), 6.13 (m, 1H), 6.40 (m, 1H).

EXAMPLE 6

9$\alpha$-fluoro-$\Delta^{4,16}$-pregnadiene-11$\beta$,21-diol-3,20-dione 3-methoxy-9-$\alpha$-fluoro-17-(isocyano-p-methylphenyl-sulfonylmethylene)-$\Delta^{3,5}$-androstadiene-11$\beta$-ol was converted to the hydroxyacetyl compound as described in Example 2 for a yield of 71% of 9$\alpha$-fluoro-$\Delta^{4,16}$-pregnadiene-11$\beta$,21-diol-3,20-dione melting after crystallization from CH$_2$Cl$_2$-petether 40°–60° C. (1:1) at 175°–186° C., $(\alpha)^{20}$ +165° C. (c 0.9, CHCl$_3$).

IR (Nujol): 3500 (OH), 1670 cm$^{-1}$ (br, C=O).

$^1$H NMR (CDCl$_3$: delta 0.7–3.7 (m), 1.23 (s), 1.57 (s), 4.17 (br. s, 1H), 4.40 (s, 2H), 5.70 (s, 1H), 6.55–6.80 (m, 1H). Litt. U.S. Pat. No. 2,963,496 discloses this compound without giving physical constants.

EXAMPLE 7

$\Delta^{4,16}$-pregnadiene-21-ol-3,11,20-trione 491 mg (1.0 mmol) of 3-methoxy-17-(isocyano-p-methylphenylsulfonylmethylene)-$\Delta^{3,5}$-androstadien-11-one were converted to the hydroxyacetyl compound as described in Example 2 with the difference that the stirring time in the first reaction step was 15 minutes for a yield of 250 mg (73%) of $\Delta^{4,6}$-pregnadiene-21-ol-3,11,20-trione melting after crystallization from CH$_2$Cl$_2$/ether, at 213°–218° C., $(\alpha)^{20}$+235° (c 1.00, CHCl$_3$).

IR (Nujol): 3420 (OH), 1710, 1675 (C=O), 1625 (C=C)cm$^{-1}$.

$^1$H NMR (CDCl$_3$): delta 0.8–3.5 (m) 0.91 (s, 1.40 (s) 4.41, 4.48 ((d, 2H), 5.68 (s, 1H), 6–64–6.83 (m, 1H). Litt. J.A.C.S. Vol. 77, p. 1028, (1955) m.p. 223°–228° C. $(\alpha)^{24}$+236° (c 1, CHCl$_3$).

EXAMPLE 8a

1$\alpha$,2$\alpha$-methylene-6-chloro-17-(2'-methoxy-3-oxazolin-4-yl)-$\Delta^{4,6,16}$-androstratrien-3-one 218 mg (0.43 mmol) of 1$\alpha$,2$\alpha$-methylene-6-chloro-17-(isocyano-p-methylphenylsulfonylmethylene)-$\Delta^{4,6}$-androstadien-3-one were dissolved in 8.6 ml of benzene and 0.17 mg of 40% formaline, 0.07 ml of methanol, 0.03 ml of Triton B and 3.44 ml of 50% aqueous NaOH solution were successively added to the benzene solution. The mixture was stirred at room temperature for half an hour and then the two layers were separated and the water layer was washed twice with 5 ml of benzene. The combined benzene layers were filtered over Al$_2$O$_3$, followed by washing with methylene chloride. After a further purification step by chromatographyl with toluene, as well as increasing quantities of acetone, 94 mg of the 1$\alpha$,2$\alpha$-methylene-6-chloro-17-(2'-methoxy-3-oxazolin-4-yl)-$\Delta^{4,6,16}$-androstratrien-3-one melting at 164–167° C. were obtained.

IR: 1655 (C(3)=O), 1630 (C=N), 1060 (COC) cm$^{-1}$.

$^1$H NMR (CDCl$_3$): delta 0.7–10 (m, cyclopropyl), 1.096 (s, 3H), 1.261 (s, 3H), 3.31 (s, 3H), 4.65 (m, 2H), 6.15 (m, 2H), 6.22 (m, 1H).

EXAMPLE 8b

1$\alpha$,2$\alpha$-methylene-6-chloro-$\Delta^{4,6,16}$-pregnatriene-21-ol-3,20-dione 90 mg of the methoxyoxazolinyl compound prepared in Example 8a were dissolved in 8 ml of THF, then 3 ml of 2N H$_2$SO$_4$ were added. The mixture was stored at room temperature for 16 hours. After addition of 540 mg (6 mmol) of NaHCO$_3$ and some water, the THF were removed by evaporation. The remaining solid substance was collected, washed with water and dried to obtain 57 mg of 1$\alpha$,2$\alpha$-methylene-6-chloro-$\Delta^{4,6,16}$-pregnatriene-21-ol-3,20-dione melting at m.p. 175°–178° C.

IR (CHCl$_3$) 1648, 1655 (c$^3$=O and C$^{20}$=O), 1588, 1608 (C=C) cm$^{-1}$.

$^1$H NMR (CDCl$_3$): delta 1.030 (s, 3H), 1.258 (s, 3H), 3.1 (s br, 1H), 4.47 (s, 2H), 6.18 (m, 2H), 6.77 (m, 1H).

EXAMPLE 9a 3,3-ethylenedithio-17-(2-methoxy-3-oxazolin-4-yl)-$\Delta^{4,16}$-androstadiene 540 mg (1 mmol) of 3,3-ethylenedithio-17-(isocyano-p-methylphenylsulfonylmethylene)-androsta-4-ene were dissolved in 20 ml of benzene and then 0.4 ml of 40% formaline, 0.4 ml of methanol, 0.4 ml of Triton B and 8 ml of 50% aqueous NaOH solution were successively added. The mixture was stirred at room temperature for 20 minutes and after dilution with water, the benzene layer was separated. The aqueous layer was extracted once with 10 ml of benzene and the collected benzene solutions were filtered over Al$_2$O$_3$ (act. II-III) and washed with CH$_2$C$_{12}$. After evaporation of the solvent, 0.5 g of 3,3-ethylenedithio-17-(2-methoxy-3-oxazolin-4-yl)-$\Delta^{4,16}$-androstadiene were obtained.

$^1$H NMR (CDCl$_3$): delta 1.01 (s, 3H), 1.07 (s, 3H), 3.33 (m, 7H), 4.3–4.9 (m, 2H), 5.53 (s, 1H), 6.30 (s, 1H), 6.59 (t, 1H).

EXAMPLE 9b 3,3-ethylenedithio-$\Delta^{4,16}$-pregnadien-21-ol-20-one 500 mg of the oxazolinyl compound prepared in Example 9a were dissolved in 10 ml of THF and 2.5 ml of 8% H$_2$SO$_4$ and the mixture was held at room temperature for 22 hours. Then, 10 ml of water were added and the THF was removed by evaporation under reduced pressure to obtain 280 mg of 3,3-ethylenedithio-$\Delta^{4,16}$-pregnadien-21-ol-20-one melting at 206°–210° C. (browning).

IR (CDCl$_3$): 3475 (OH), 1665 (C=O), 1586 (delta$^{16}$) cm$^{-1}$.

$^1$HNMR (CDCl$_3$): delta 0.95 (s, 3H), 1.06 (s, 3H), 3.32 (S, 4H), 4.46 (s, 2H), 5.50 (s, 1H), 6.76 (t, 1H).

EXAMPLE 10a 3,3-ethylenedioxy-17-(2'-methoxy-3-oxazolin-4-yl)-$\Delta^{5,16}$- and-rostadiene 507 mg (1 mmol) of 3,3-ethylenedioxy-17-(isocyano-p-methylphenylsulfonylmethylene)-$\Delta^5$-androstaene were dissolved in 20 ml of benzene and then 0.4 ml of 40% formaline, 0.4 ml of methanol, 0.06 ml of Triton B and 8 ml of 50% aqueous NaOH solution were added. The reaction mixture was stirred for half an hour at room temperature and then the water layer was separated and washed twice with benzene. The combined benzene layers were filtered over Al$_2$O$_3$ (act. II–III), layer thickness 3.5 cm, and washed with CH$_2$Cl$_2$. The solvent was evaporated to obtain 296 mg (72% yield) of 3,3-ethylenedioxy-17-(2'-methoxy-3-oxazolin-4-yl)-$\Delta^{5,16}$-androstadiene in the form of a while solid melting at 154°–157° C.

IR (CHCl$_3$): 1623 (C=N), 1093 (C—0—C) cm$^{-1}$.

$^1$H MNR (CDCl$_3$): delta 1.017 (s, 3H), 1.077 (s, 3H), 3.29, 3,39 (2 xs, 6H), 3.92 (s, 4H), 4.66 (m, 2H), 5.35 (m, 1H), 6.27 (m, 1H), 6.54 (t, 1H).

EXAMPLE 10b $\Delta^{4,16}$-pregnadiene-21-ol-3,20-dione 222 mg of the oxazolinyl compound prepared in Example 10a were dissolved in 15 ml of THF and then 4.5 ml of 2N H$_2$SO$_4$ were added. The solution was kept for 16 hours at room temperature and the THF was evaporated. The remaining solid was washed with water and dried under reduced pressure to obtain 178 mg of product in which hydrolysis was not yet complete. Therefore, a further reaction with 4N $H_2SO_4$ in THF was used resulting in 162 mg (92%) of pure $\Delta^{4,16}$-pregnadiene-21-ol-3,20-dione. IR and NMR were identical with the spectra of the product obtained in Example 1b.

EXAMPLE 11a

3β-(2'-tetrahydropyranyloxy)-17-(2-methoxy-3-oxazolin-4-yl)-$\Delta^{5,16}$-androstadiene 570 mg (1.04 mmol) of 3-(2'β-tetrahydropyranyloxy)-17-(isocyano-p-methylphenylsulfonylmethylene) -$\Delta^5$-androstaene were dissolved in 21 ml of benzene and then 0.42 ml of formaline, 0.42 ml of methanol, 0.062 ml of Triton B and 8.3 ml of an aqueous 50% NaOH solution were added. The reaction mixture was stirred at room temperature for 25 minutes and the benzene layer was separated. The water layer was washed with two portions of 5 ml of benzene and the combined benzene solutions were filtered over $Al_2O_3$ (act. II–III) and washed with 100 ml of $CH_2Cl_2$. After evaporation of the solvent, 330 mg of the 3β-(2'-tetrahydropyranyloxy)-17-(2-methoxy-3-oxazolin-4-yl)-$\Delta^{5,16}$-androstadiene were obtained.

IR ($CHCl_3$): 1623 (C=N), 1055, 1025 (C—0—C).

$^1$H NMR ($CDCl_3$): delta 1.017 (s, 3H), 5.30 (m, 1H), 6.22 (m, 1H), 6.48 (m, 1H).

EXAMPLE 11b $\Delta^{5,16}$-pregnadien-3β,21-diol-20-one 152 mg (0.27 mmol) of the oxazolinyl compound prepared in Example 11a were dissolved in 12 ml of THF and then 3.5 ml of 4N $H_2SO_4$ were added. After storage at room temperature for 20 hours, 1.359 (16 mmol) of $NaHCO_3$ and 25 ml of water were added. The THF was evaporated and the remaining solid was collected, washed with water and dried. Column-purification using toluene-acetone (9:1) yielded 64 mg of pure $\Delta^{5,16}$-pregnadien-3β,21-diol-20-one melting at 194°–197° C. (browning at 187° C.).

IR ($CHCl_3$): 3610, 3470 (OH), 1666 ($C^{20}$=0), 1585 (C=C) cm$^{-1}$.

$^1$H NMR ($CDCl_3$): delta 0.96 (s, 3H), 1.03 (s, 3H), 3.18 (s, 1H), 3.35 (m, 1H), 4.33 (m, 2H), 5.24 (m, 1H), 6.74 ($C^{16}$H).

EXAMPLE 12a 3-methoxy-17-(2'-methoxy-3-oxazolin-4-yl)-$\Delta^{3,5,16}$-androstatriene-11β-ol To a solution of 496 g (1 mmol) of 3-methoxy-17-(isocyano-p-methylphenylsulfonylmethylene)-$\Delta^{3,5}$-androstadiene-11β-ol in 20 ml of toluene were added 300 mg (10 mmol) of paraformaldehyde, 0.8 ml of methanol, 25 mg of benzyltriethyl ammonium chloride and 8 ml of 50% aqueous NaOH solution. The mixture was stirred vigorously for 25 minutes and was extracted with toluene. The organic phase was filtered over $Al_2O_3$ (act. II–III), followed by a washing with methylene chloride and evaporation in vacuo yielded 196 mg of 3-methoxy-17-(2'methoxy-3-oxazolin-4-yl)-$\Delta^{3,5,16}$-and-rostatriene-11β-ol.

IR ($CHCl_3$): 1653, 1623 (C=C=C=N) cm$^{-1}$.

$^1$H NMR ($CDCl_3$): delta 1.048 (s, 3H), 1.174 (s, 3H), 3.35 (s, 3H), 3.57 (s, 3H), 4.20 (m, 1H), 4.70 (m, 2H), 5.14 (s, 1H), 5.76 (m, 1H), 6.32 (tr, 1H), 6.57 (m, 1H).

EXAMPLE 12b $\Delta^{4,16}$-pregnadiene-11α,21-diol-3,20-dione 98 mg of the oxazolinyl compound prepared in Example 12a were dissolved in 5 ml of THF and then 1.25 ml of 4N $H_2SO_4$ were added. After storage at room temperature for 20 hours, 5 ml of water were added and the THF was evaporated. The remaining substance was collected to obtain a yield of 69 mg of $\Delta^{4,16}$-pregnadiene-11α,21-diol-3,20-dione.

IR ($CHCl_3$): 3598 (OH), 3470 (OH), 1660 (C=0), 1615, 1589 (C=C) cm$^{-1}$.

$^1$H NMR ($CDCl_3$): delta 0.996 (s, 3H), 1.271 (s, 3H), 4.20 (m, 1H), 4.48 (s, 2H), 5.77 (s, 1H), 6.80 (tr. 1H).

EXAMPLE 13a 3-methoxy-6-chloro-17-(2-methoxy-3-oxazolin-4-yl)-$\Delta^{3,5,16}$-and-rostatriene To a solution of 1 g of 3-methoxy-6-chloro-17-(isocyano-p-methylphenylsulfonylmethylene)-$\Delta^{3,5}$-androstadiene in 50 ml of toluene were added 1 ml of methanol, 1 ml of 40% formaline, 75 mg of benzyltriethyl ammonium chloride and 20 ml of aqueous 50% NaOH solution. The mixture was stirred vigorously for 1.5 hours at ambient temperature and was extracted with toluene. The organic phase was filtered over $Al_2O_3$ (act. II–III) followed by washing with methylene chloride. Evaporation yielded 0.49 g of 3-methoxy-6-chloro-17-(2-methoxy-3-oxazolin-4-yl)-$\Delta^{3,5,16}$-androstatriene.

IR ($CHCl_3$): 1643, 1619 (C=C+N=C) cm$^{-1}$.

$^1$H NMR ($CDCl_3$): delta 1.047 (s, 6H), 3.36 (s, 3H), 3.65 (s, 3H), 4.71 (m, 2H), 5,67 (s, 1H), 6.32 (tr, 1H), 6.58 (tr, 1H).

EXAMPLE 13b 3-methoxy-6-chloro-$\Delta^{3,5,16}$-pregnatrien-21-ol-20-one 400 mg of the oxazolinyl compound prepared in Example 13a were dissolved in 20 ml of THF and then 5 ml of THF were added. After storage at ambient temperature for 18 hours, 20 ml of water were added and the THF was evaporated. The resulting substance was extracted with methylene chloride and the organic layer was dried and concentrated to dryness. Column purification using toluene yielded 120 mg of pure 3-methoxy-6-chloro-$\Delta^{3,5,16}$-pregnatrien-21-ol-20-one melting at 158°–160° C.

IR ($CHCl_3$): 3471 (OH), 1670 (C=0), 1645, 1620, 1588 (C=C) cm$^{-1}$.

$^1$H NMR ($CDCl_3$): delta 0.983 (s, 3H), 1.044 (s, 3H), 3.65 (s, 3H), 4.48 (s, 2H), 5.66 (s, 1H), 6.78 (tr, 1H).

EXAMPLE 14a

3β-methoxymethoxy-17-(2'-methoxy-3-oxazolin-4-yl)-$\Delta$5,16-androstadiene 509 mg of 3β-methoxymethoxy-17-(isocyano-p-methylphenylsulfonyl-methylene)-$\Delta^{5,16}$-androstadiene were converted to 193 mg of 3β-methoxymethoxy-17-(2'-methoxy-3-oxazolin-4-yl)-$\Delta^{5,16}$-androstadiene as described in Example 13a with the difference that the mixture was stirred for 35 minutes.

$^1$H NMR ($CDCl_3$): delta, 0.99 (s, 3H), 1.04 (s, 3H), 3.33 (s, 7H), 4.65 (m, 4H), 5.35 (m, 1H), 6.35 (m, 1H), 6.53 (m, 1H).

EXAMPLE 14b

3β-methoxymethyl-Δ$^{5,16}$-pregnadiene-21-ol-20-one 103 mg of the oxazolinyl compound prepared in Example 14a were dissolved in 6 ml of THF and then 1.5 ml of 2N H$_2$SO$_4$ were added. After storage at room temperature for 48 hours, 15 ml of water were added and the THF was removed by evaporation in vacuo. The precipitated solid was collected, washed with water and dried to obtain 37 mg of 3β-methoxymethoxy-Δ5,16-pregnadiene-21-ol-20-one.

$^1$H NMR (CDCl$_3$): delta 0.95 (s, 3H), 1.05 (s, 3H), 3.34 (s, 4H), 4.42 (s, 2H), 4.64 (s, 2H), 5.35 (m, 1H), 6.71 (m, 1H).

EXAMPLE 15a 17-(2'methoxy-3-oxazolin-4-yl)-Δ$^{4,16}$-androstadien-3-one 200 mg of 17-(isocyano-p-methylphenylsulfonylmethylene)-Δ$^4$-androsten-3-one were converted to 120 mg of 17-(2'-methoxy-3-oxazolin-4-yl)-Δ$^{4,16}$-androstadien-3-one as described in Example 1a with the difference that the mixture was stirred for 20 minutes.

$^1$H NMR (CDCl$_3$): delta 0.99 (s, 3H), 1.18 (s, 3H), 3.28 (s, 3H), 4.46 (m, 2H), 5.68 (s, 1H), 6.23 (m, 1H), 6.49 (m, 1H).

EXAMPLE 15b

Δ$^{4,16}$-pregnadiene-21-ol-3,20-dione 120 mg of the oxazolinyl compound prepared in Example 15a were converted to 37 mg of Δ$^{4,16}$-pregnadiene-21-ol-3,20-dione as described in Example 14b. IR and NMR were identical with the spectra of the products obtained in Examples 1b and 10b.

EXAMPLE 16

19-nor-Δ$^{4,16}$-pregnadiene-21-ol-3,20-dione

To a solution of 351 mg of 3-methoxy-17-(isocyano-p-methylphenylsulfonylmethylene)-19-nor-Δ$^{3,5}$-androstadiene in 15 ml of toluene were added 0.3 ml of 40% formaline, 0.3 ml of methanol, 22 mg of benzyltriethyl ammonium chloride and 6 ml of 50% aqueous NaOH solution and the mixture was stirred vigorously for 65 minutes at ambient temperature. The mixture was extracted with toluene and the organic phase filtered over Al$_2$O$_3$ (act. II–III) followed by washing with methylene chloride. Evaporation in vacuo yielded 112 mg of 3-methoxy-17-(2-methoxy-3-oxazolin-4'-yl)-19-nor-Δ$^{3,5,16}$-androstatriene. Without further processing, this oxazolinyl compound was hydrolyzed by dissolving it in 8 ml of THF and 2 ml of H$_2$SO$_4$. After stirring for 17 hours at room temperature, 20 ml of water were added and the THF was removed by evaporation in vacuo. The precipitated solid was collected, washed with water and dried to obtain 58 mg of 19-nor-Δ$^{4,16}$-pregnadiene-21-ol-3,20-dione.

IR (CHCl$_3$): 3475 (OH), 1666 (C=O), 1619, 1588 (C=C) cm$^{-1}$.

$^1$H NMR (CDCl$_3$): delta 1.02 (s, 3H), 3.24 (s, 1H), 4.48 (s, 2H), 5.87 (s, 1H), 6.78 (tr, 1H).

EXAMPLE 17

1α-methyl-3-methoxy-17-(2-methoxy-3-oxazolin-4-yl)-Δ$^{3,5,16}$-androstatriene 653 mg (83% yield) of 1α-methyl-3-methoxy-17-(2-methoxy-3-oxazolin-4-yl)-Δ$^{3,5,16}$-androstatriene were prepared as described in Example 9a, starting from 982 mg (2 mmol of 1α-methyl-3-methoxy-17-(isocyano-p-methylphenylsulfonylmethylene)-Δ$^{3,5}$-androstadiene.

IR (CHCl$_3$): 1628 (C=N), 1057 (COC).

$^1$H NMR (CDCl$_3$): delta 0.78 (d, 3H), 1.03 (s, 3H), 1.07 (s, 3H), 3.30 (s, 3H), 3.52 (s, 3H), 4.65 (m, 2H), 5.06 (m, 1H), 5.29 (m, 1H), 6.25 (m, 1H), 6.52 (m, 1H). In the same way as described in Example 9b, the said compound was hydrolyzed to 1α-methyl-Δ$^{4,16}$-pregnadiene-21-ol-3,20-dione.

EXAMPLE 18

3-methoxy-17-(2'-methoxy-3-oxazolin-4-yl)-Δ$^{3,5,16}$-androstatriene

Using the method of Example 2, 3-methoxy-17-(2'-methoxy-3-oxazolin-4-yl)-Δ$^{3,5,16}$-androstatriene was prepared from a number of 3-methoxy-17-(isocyano-sulfonylmethylene)-Δ$^{3,5}$-androstadienes with different groups attached to the sulfonyl group. The following results were obtained.

| R | Yield |
|---|---|
| —C$_6$H$_4$CH$_3$ | 92% |
| —C$_6$H$_4$—OCH$_3$ | 82% |
| —C$_6$H$_4$—p-Cl | 97% |
| —n-(CH)$_9$CH$_3$ | 86% |
| —t-C$_4$H$_9$ | 6% |
| —CH$_3$ | 90% |

EXAMPLE 19

3-methoxy-17-(2'-allyloxy-3-oxazolin-4-yl)-Δ$^{3,5,16}$-androstatriene 350 mg (86% yield) of 3-methoxy-17-(2'-allyloxy-3-oxazolin-4-yl)-Δ$^{3,5,16}$-androstatriene were prepared by the method described in Example 2, starting from 477 mg of the α,β-unsaturated-isocyanide and using 0.5 ml (7 mmol) of allylalcohol instead of methanol.

IR (Nujol): 1655, 1630, $^1$H NMR (CDCl$_3$): delta 0.8–2.8 (m), 1.0 (s, 6H), 3.5 (s, 3H), 3.98, 4.18, (d, 2H), 4.5–4.7 (m, 2H), 3.9–4.4 (m, 4H), 4.5–6.05 (m, 1H), 6.05–6.3 (m, 1H), 6.3–0.6 (m, 1H).

EXAMPLE 20

3-methoxy-17-(2'-methoxymethoxy-3-oxazolin-4-yl)-Δ$^{3,5,16}$-androstatriene 239 mg (0.5 mmol) of 3-methoxy-17-(isocyano-p-methylphenylsulfonylmethylene)-Δ$^{3,5}$-androstadiene were dissolved in 7.5 ml of benzene and 2.5 mmol (100 mg) of sodium hydroxide, 0.10 ml (0.5 mmol) of 15-crown-5, 150 mg (5 mmol) of paraformaldehyde and 0.2 ml of methanol were added. After stirring for 3.5 hours, 3-methoxy-17-(2'-methoxymethoxy-3-oxazolin-4-yl)-Δ$^{3,5,16}$-androstatriene was isolated from the reaction mixture in the usual way in a yield of 96%.

IR (Nujol): 1625 cm$^{-1}$.

$^1$H NMR (CDCl$_3$): delta 0.9–2.8 (m), 1.82 (s, 3H), 3.42 (s, 3H), 3.55 (s, 3H), 4.6–5.05 (m, 4H), 5.1–5.4 (m, 2H), 6.2–6.4 (m, 1H), 6.6–6.9 (m, 1H). M.p. 145°–165° C. (CH$_2$Cl$_2$/MeOH).

Analysis: C$_{25}$H$_{35}$NO$_4$: molecular weight=413.563 Calculated: % C 72.61 % H 8.53 % N 3.39. Found: 72.3 8.7 3.4.

EXAMPLE 21a 3-isobutoxy-17-(2-methoxy-3-oxazolin-4-yl)-Δ$^{3,5}$-androstatriene 520 mg (1 mmol) of 3-isobutoxy-17-(isocyano-p-methylphenylsulfonylmethylene)-$\Delta^{3,5}$-androstadiene were converted to 240 mg of 3-isobutoxy-17-(2-methoxy-3-oxazolin-4-yl)-$\Delta^{3,5}$-androstatriene as described in Example 13a with the difference that tetrabutylammonium tetrafluorborate was used as phase transfer catalyst.

$^1$H NMR (CDCl$_3$): delta 0.95 ppm, (d, 6H), 1.046 (s, 6H), 3.34 (s, 3H), 3.47 (d, 2H), 4.70 (m, 2H), 5.12 (s, 1H), 5.18 (tr, 1H), 6.30 (tr, 1H), 6.57 (tr, 1H).

EXAMPLE 21b $\Delta^{4,16}$-pregnadiene-21-ol-3,20-dione 192 mg of the oxazolinyl compound prepared in Example 21a were converted to 119 (73% yield) of $\Delta^{4,16}$-pregnadiene-21-ol-3,20-dione as described in Example 1b. IR was identical with the IR of the product obtained in Example 1b.

EXAMPLE 22a 3-methoxy-17-(2-methoxy-3-oxazolin-4-yl)-$\Delta^{3,5,16}$-androstatriene-9$\alpha$-ol 494 mg (1 mmol) of 3-methoxy-17-(isocyano-p-methylphenylsulfonylmethylene)-$\Delta^{3,5}$-androstadiene-9$\alpha$-ol were converted to 170 mg of 3-methoxy-17-(2-methoxy-3-oxazolin-4-yl)-$\Delta^{3,5,16}$-androstatriene-9$\alpha$-ol as described in Example 13a.

$^1$H NMR (CDCl$_3$): delta 1.045 ppm (s, 3H), 1.146 (s, 3H), 3,36 (s, 3H), 3.58 (s, 3H), 4.70 (m, 2H), 5.17 (s, 1H), 5.31 (tr, 1H), 6.30 (tr, 1H), 6.57 (d, 1H).

EXAMPLE 22b $\Delta^{4,16}$-pregnadiene-9$\alpha$,21-diol-3,20-dione 97 mg of the oxazolinyl compound of Example 22a were dissolved in 6 ml of THF and 1.5 ml of 2N H$_2$SO$_4$ and the mixture was held at room temperature for 22 hours. Then, 10 ml of water were added and the THF was removed by evaporation under reduced pressure to obtain 34 mg of $\Delta^{4,16}$-pregnadiene-9$\alpha$,21-diol-3,20-dione.

IR (KBr): 3400 (OH) 1664 (C=0, 2x) 1612 1579 (C=C).

$^1$H (CDCl$_3$): 0.992 (s, 3H), 1.369 (s, 3H), 2.95 (br, s, OH), 3.58 (br, s, OH), 4.40–4.54 (AB, 2H), 5.81 (s, 1H), 6.81 (tr, 1H).

EXAMPLE 23

$\Delta^{4,16}$-pregnadiene-21-ol-3,20-dione 840 mg (7.5 mmol) of potassium t-butoxide were added to 25 ml of dry tetrahydrofuran whereafter the suspension was cooled to $-70°$ C. 1.17 g (6 mmol) of TosMIC dissolved in 10 ml of THF were added to the suspension and after 10 minutes of stirring at $-70°$ C., 1.5 g (5 mmol) of 3-methoxyandrosta-3,5-dien-17-one dissolved in 15 ml of THF was added. The mixture was stirred for two hours at $-40°/-30°$ C., followed by the addition of 0.64 g (7.5 mmol) of phosphoric acid at $-35°$ C. After stirring for 10 minutes, 7.5 (54 mmol) of triethylamine and 1 ml (11 mmol) of phosphoroxy trichloride were added at $-35°$ C. The reaction mixture was stirred for one hour at 0° C. and 2 ml of 36% formaline, 2 ml of methanol and 7 g of powered KOH were added. After stirring for 20 minutes, the reaction mixture was filtered and 20 ml of 4N sulfuric acid were added, followed by 10 ml of THF. After stirring for 20 hours, the THF was evaporated in vacuo and the crystals were successively dried, washed with water and dried to obtain 1.22 g (74% yield) of $\Delta^{4,16}$-pregnadiene-21-ol-3,20-dione which was identical with the compound of Example 16.

EXAMPLE 24

3-Methoxy-17-(2'-benzyloxy-3-oxazolin-4-yl)androsta-3,5,16-triene.

3-Methoxy-17-(2'-benzyloxy-3-oxazolin-4-yl)androsta-3,5,16-triene was prepared in the same way as described in Example 19, however, using benzylalcohol (1 ml, 10 mmol) instead of allylalcohol. Yield: 52%, m.p. 115°–125° C.

IR (Nujol): 1630 (N=C).

$^1$H NMR CDCl$_3$: delta 0.8–2.8 (m), 1.06 (s), 3.58 (s, 3H), 4.55–4.9 (m, 4H), 4.65 (s), 5.1–5.4 (m, 2H), 6.15–6.45 (m, 1H), 7.34 (s, 5H). Exact mass 459.276 (calcd. 459.277).

Various modifications of the products and process of the invention may be made without departing from the spirit or scope thereof and it is to be understood that the invention is intended to be limited only as defined in the appended claims.

What we claim is:

1. A process for the preparation of 21-hydroxy-20-keto-$\Delta^{16}$-steroids comprising reacting a 17-(isocyanosulfonylmethylene)-steroid with an aldehyde and an alcohol to form a 17-(2-alkoxy-3-oxazolin-4-yl)-$\Delta^{16}$-steroid and subjecting the latter to hydrolysis to obtain the corresponding 21-hydroxy-20-keto-$\Delta^{16}$steroid.

2. The process of claim 1 wherein the first reaction is effected in the presence of a base.

3. The process of claim 2 wherein the base is selected from the group consisting of alkali metal hydroxide, alkali metal alcoholate, phosphonium hydroxide and quaternary ammonium hydroxides and is effected in an inert organic solvent.

4. The process of claim 3 wherein a catalyst selected from the group consisting of phosphonium salt, a crown ether and a quaternary ammonium salt is added to the reaction.

5. The process of claim 2 effected under phase-tranfer conditions.

6. The process of claim 1 wherein the aldehyde is selected from the group consisting of a phenylaldehyde optionally substituted with at least one member of the group consisting of halogen and alkyl and alkoxy of 1 to 4 carbon atoms, and alkyl aldehyde of 1 to 4 carbon atoms optionally substituted with at least one member of the group consisting of halogen and alkoxy of 1 to 4 carbon atoms.

7. The process of claim 1 wherein the aldehyde is acetaldehyde or benzaldehyde.

8. The process of claim 1 wherein the aldehyde is formaldehyde.

9. The process of claim 1 wherein the alcohol is selected from the group consisting of arylalkyl alcohols and alkyl alcohols.

10. The process of claim 1 wherein the alcohol is an alkyl alcohol of 1 to 6 carbon atoms.

11. The process of claim 1 wherein the alcohol is methanol or ethanol.

12. The process of claim 1 wherein the hydrolysis is effected in an organic solvent in the presence of an aqueous acid.

13. The process of claim 1 wherein the 17-(isocyanosulfonylmethylene)-steroid have the formula

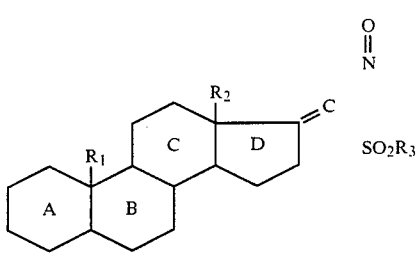

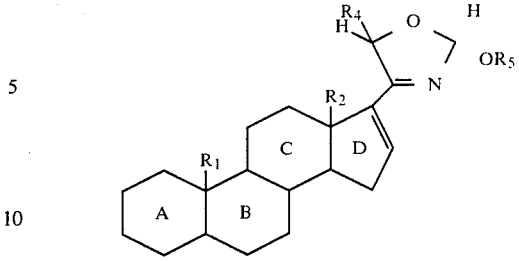

wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 6 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms.

14. The process of claim 13 wherein $R_3$ is selected from the group consisting of alkyl of 1 to 10 carbon atoms and phenyl and naphthyl optionally substituted with at least one member of the group consisting of halogen, alkyl of 1 to 6 carbon atoms and alkoxy of 1 to 6 carbon atoms.

15. The process of claim 13 wherein $R_3$ is selected from the group consisting of phenyl, p-methoxyphenyl and p-methylphenyl.

16. The process of claim 13 having at least one double bond selected from the group consisting of 1(2), 3(4), 4(5), 5(6), 6(7), 9(11) and 11(12).

17. The process of claim 13 having at least one substitutent selected from the group consisting of hydroxy at 3-, 9-, 11-, 12- and 14-positions, keto in the 6-, 9- and 11-positions, fluorine, chlorine and bromine in the 6-, 9- and 11-positions, methyl in the 1- and 6-positions, alkoxy of 1 to 4 carbon atoms in the 3-, 9- and 11-positions and alkoxyalkoxy of 2 to 6 carbon atoms in the 3- and 11-positions.

18. The process of claim 13 having at least one substituent selected from the group consisting of 1,2-epoxy, 9,11-epoxy, 1,2-methylene and 3,3-alkylenedioxy, 3,3-alkylenedithio and 3,3-alkyleneoxythio of 1 to 4 alkylene carbon atoms.

19. A process for the preparation of a 17-(2-alkoxy-3-oxazolin-4-yl)-$^{16}$-steroid of the formula wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 6 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms comprising reacting a compound of the formula

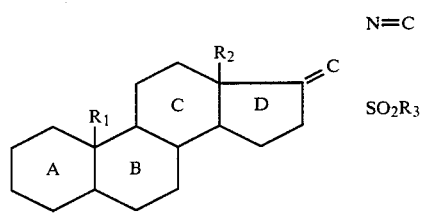

wherein the steroid is defined as above with an aldehyde and an alcohol under basic conditions.

20. The process of claim 19 wherein the base is selected from the group consisting of alkali metal hydroxide, alkali metal alcoholate, phosphonium hydroxide and quaternary ammonium hydroxides and is effected in an inert organic solvent.

21. The process of claim 20 wherein a catalyst selected from the group consisting of phosphonium salt, a crown ether and a quaternary ammonium salt is added to the reaction.

22. The process of claim 20 effected under phase-transfer conditions.

23. The process of claim 19 wherein the aldehyde is selected from the group consisting of phenylaldehyde optionally substituted with at least one member of the group consisting of halogen and alkyl and alkoxy of 1 to 4 carbon atoms and alkyl aldehyde of 1 to 4 carbon atoms, optionally substituted with at least one member of the group consisting of halogen and alkoxy of 1 to 4 carbon atoms.

24. The process of claim 19 wherein the aldehyde is acetaldehyde or benzaldehyde.

25. The process of claim 19 wherein the aldehyde is formaldehyde.

26. The process of claim 19 wherein the alcohol is selected from the group consisting of arylalkyl alcohols and alkyl alcohols.

27. The process of claim 19 wherein the alcohol is an alkyl alcohol of 1 to 6 carbon atoms.

28. The process of claim 19 wherein the alcohol is methanol or ethanol.

29. A compound of the formula

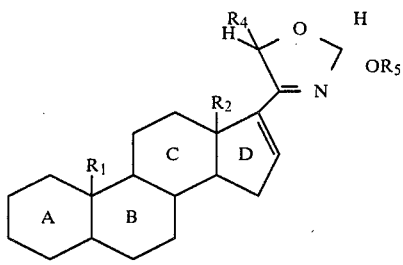

wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 6 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms.

30. A process for the preparation of 21-hydroxy-20-keto-$\Delta^{16}$-steriods comprising hydrolysing a 17-(2-alkoxy-3-oxazolin-4-yl)$\Delta^{16}$-steroid.

* * * * *

UNITED STATES PATENT AND TRADEMARK OFFICE
CERTIFICATE OF CORRECTION

PATENT NO. : 4,548,749

DATED : Oct. 22, 1985

INVENTOR(S) : Albert M. van Leusen, Adriaan M. van Leusen

Page 1 of 4

It is certified that error appears in the above-identified patent and that said Letters Patent are hereby corrected as shown below:

| Col. | Line | |
|---|---|---|
| 2 | 6 | The Invention should be in the center and "The novel process etc. should start a new paragraph |
| 2 | 25 | 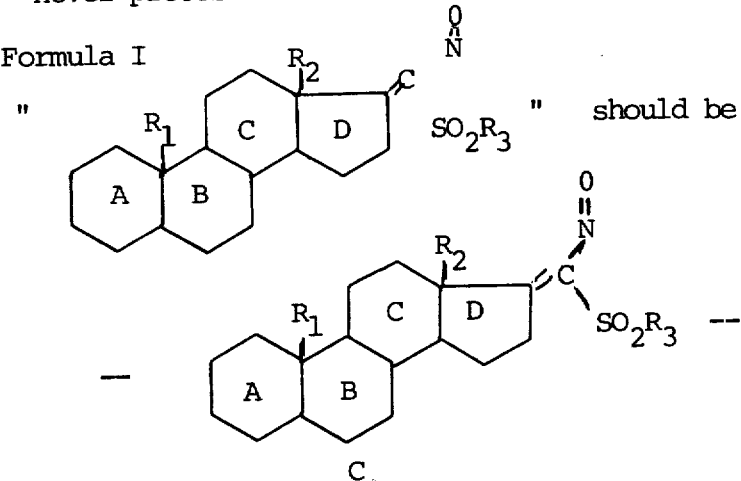 |
| 3 | 5 | 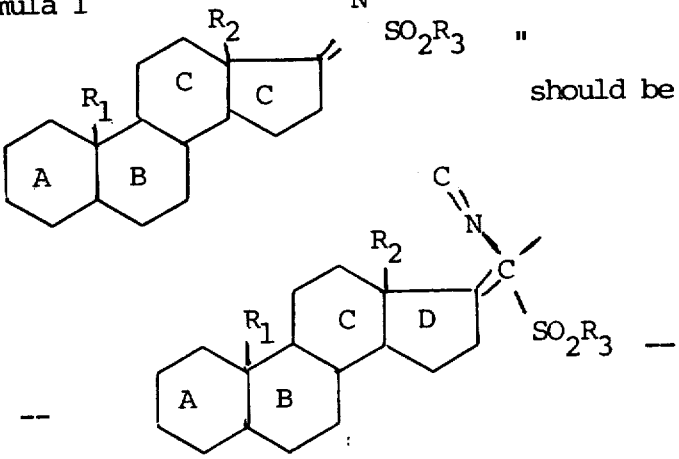 |

UNITED STATES PATENT AND TRADEMARK OFFICE
CERTIFICATE OF CORRECTION

PATENT NO. : 4,548,749

DATED : Oct. 22, 1985

INVENTOR(S) : Albert M. van Leusen, Adriaan M. van Leusen

It is certified that error appears in the above-identified patent and that said Letters Patent are hereby corrected as shown below:

| Col. | Line | | |
|---|---|---|---|
| 10 | 18 | "$CH_2Cl_{12}$" should be | --$CH_2Cl_2$-- |
| 12 | Example 14a | "$\Delta 5,16$" should be | --$\Delta^{5,16}$-- |
| 17 | Claim 13 | 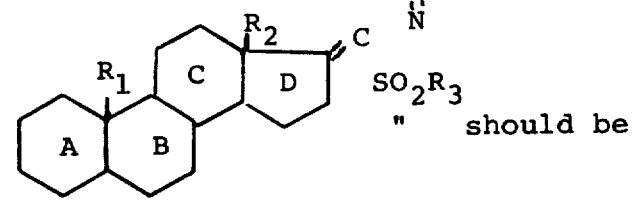 should be 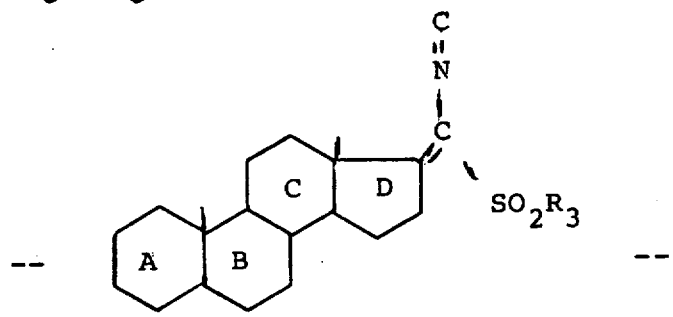 | |

UNITED STATES PATENT AND TRADEMARK OFFICE
CERTIFICATE OF CORRECTION

PATENT NO. : 4,548,749
DATED : Oct. 22, 1985
INVENTOR(S) : Albert M. van Leusen, Adriaan M. van Leusen It is certified that error appears in the above-identified patent and that said Letters Patent are hereby corrected as shown below:

| Col. | Line |
|---|---|
| 18 | Claim 19 |

" 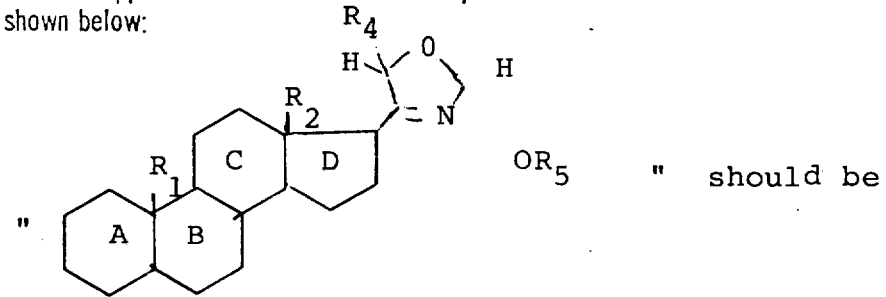 should be

-- 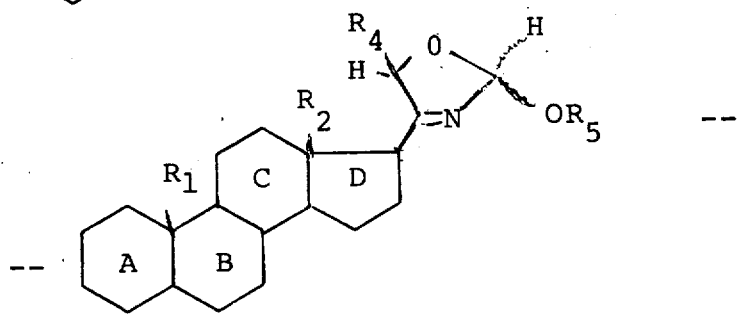 --

| 18 | Claim 19 |
|---|---|

" 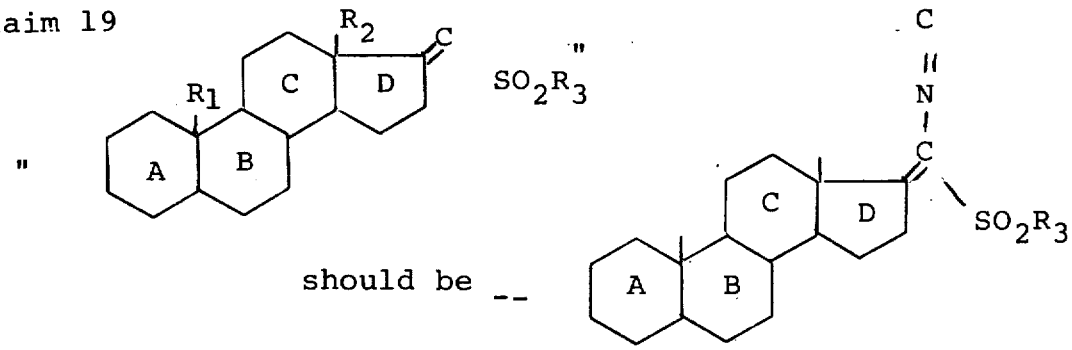 should be --

UNITED STATES PATENT AND TRADEMARK OFFICE
CERTIFICATE OF CORRECTION

PATENT NO. : 4,548,749
DATED : Oct. 22, 1985
INVENTOR(S) : Albert M. van Leusen, Adriaan M. van Leusen It is certified that error appears in the above-identified patent and that said Letters Patent are hereby corrected as shown below:

Col. Line
19   Claim 29

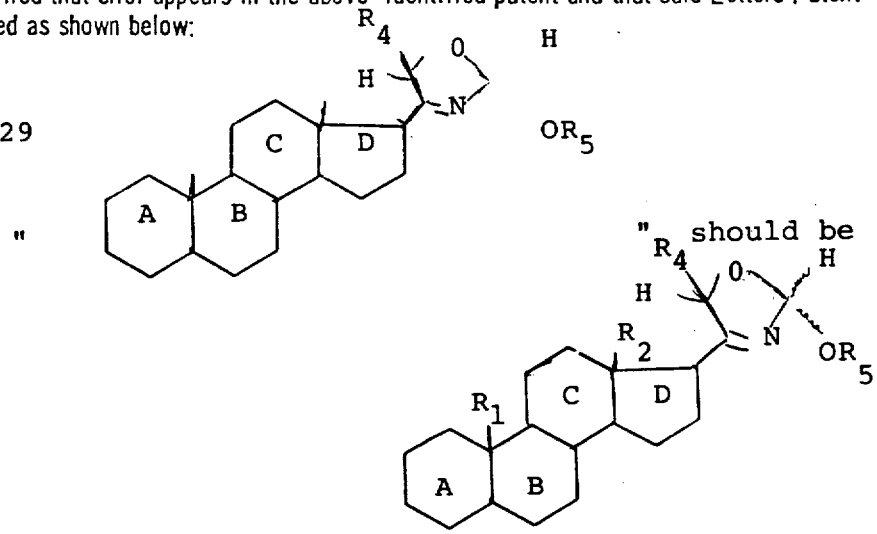

Signed and Sealed this

Fourth Day of November, 1986

[SEAL]

Attest:

Attesting Officer

DONALD J. QUIGG
Commissioner of Patents and Trademarks

UNITED STATES PATENT AND TRADEMARK OFFICE
CERTIFICATE OF CORRECTION

PATENT NO. : 4,548,749

DATED : Oct. 22, 1985

INVENTOR(S) : Albert M. vanLeusen and Adriaan M. vanLeusen

It is certified that error appears in the above-identified patent and that said Letters Patent is hereby corrected as shown below:

Col. 2, line 25, the formula should read:

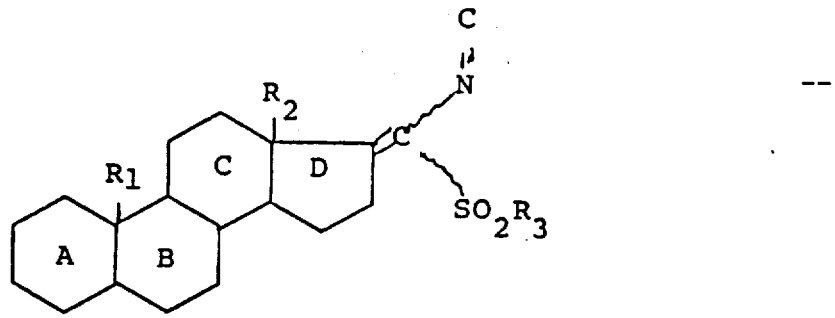

Col. 3, line 5, the formula should read:

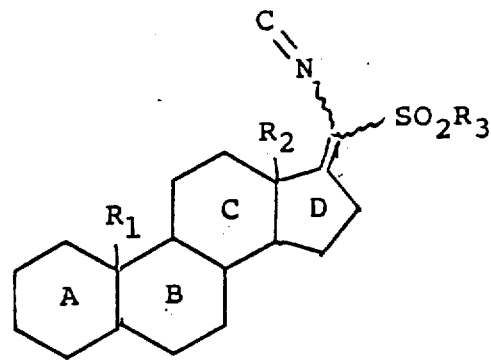

UNITED STATES PATENT AND TRADEMARK OFFICE
CERTIFICATE OF CORRECTION

PATENT NO. : 4,548,749
DATED : Oct. 22, 1985
INVENTOR(S) : ALBERT M. vanLEUSEN and ADRIAAN M. vanLEUSEN It is certified that error appears in the above-identified patent and that said Letters Patent is hereby corrected as shown below:

Col. 17, claim 13, line 3, the formula should read:

-- 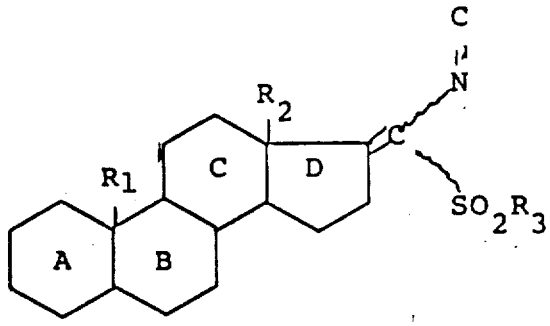 --

Col. 18, claim 19, line 5, the formula should read:

-- 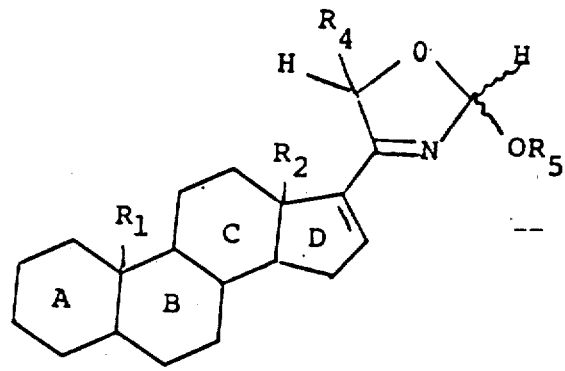 --

UNITED STATES PATENT AND TRADEMARK OFFICE
CERTIFICATE OF CORRECTION

PATENT NO. : 4,548,749

DATED : Oct. 22, 1985

INVENTOR(S) : ALBERT M. vanLEUSEN and ADRIAAN M. vanLEUSEN

It is certified that error appears in the above-identified patent and that said Letters Patent is hereby corrected as shown below:

Col. 18, claim 19, line 35, the formula should read:

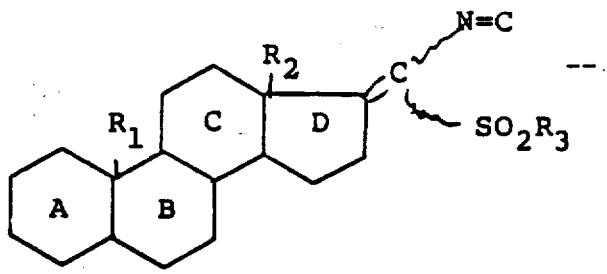

Col. 19, clm. 29 line 10, the formula should read:

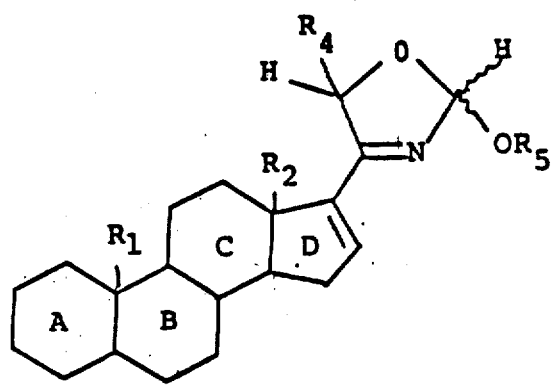

Signed and Sealed this

Fifteenth Day of March, 1988

Attest:

DONALD J. QUIGG

Attesting Officer

Commissioner of Patents and Trademarks